United States Patent [19]

Reiter

[11] 4,436,820
[45] Mar. 13, 1984

[54] METHOD AND APPARATUS FOR GLYCOSYLATED HEMOGLOBIN SEPARATING AND MEASURING FRACTIONS

[76] Inventor: Paul C. Reiter, 20 Celia St., Port Jefferson Station, N.Y. 11776

[21] Appl. No.: 344,404

[22] Filed: Feb. 1, 1982

[51] Int. Cl.³ .............................................. G01N 33/72
[52] U.S. Cl. ...................................... 436/67; 210/789; 210/927; 422/61; 422/72; 436/178
[58] Field of Search ................... 436/67, 178; 210/789, 210/927; 422/61, 72

[56] References Cited

U.S. PATENT DOCUMENTS

| | | | |
|---|---|---|---|
| 3,963,119 | 6/1976 | Lukacs et al. | 210/927 X |
| 4,243,534 | 1/1981 | Bulbenko | 436/67 X |
| 4,268,270 | 5/1981 | Gabbay et al. | 436/67 |
| 4,269,605 | 5/1981 | Dean et al. | 436/67 |
| 4,270,921 | 6/1981 | Graas | 436/67 |

*Primary Examiner*—Arnold Turk
*Attorney, Agent, or Firm*—Stephen E. Feldman

[57] ABSTRACT

Method and apparatus for separating and measuring the amount of the glycosylated hemoglobin fractions in a blood sample. The method and apparatus provide a means for lysing sample red blood cells and, in the same container, separating the glycosylated hemoglobin fractions from the other residual hemoglobin fractions through the utilization of a polymeric material.

37 Claims, 6 Drawing Figures

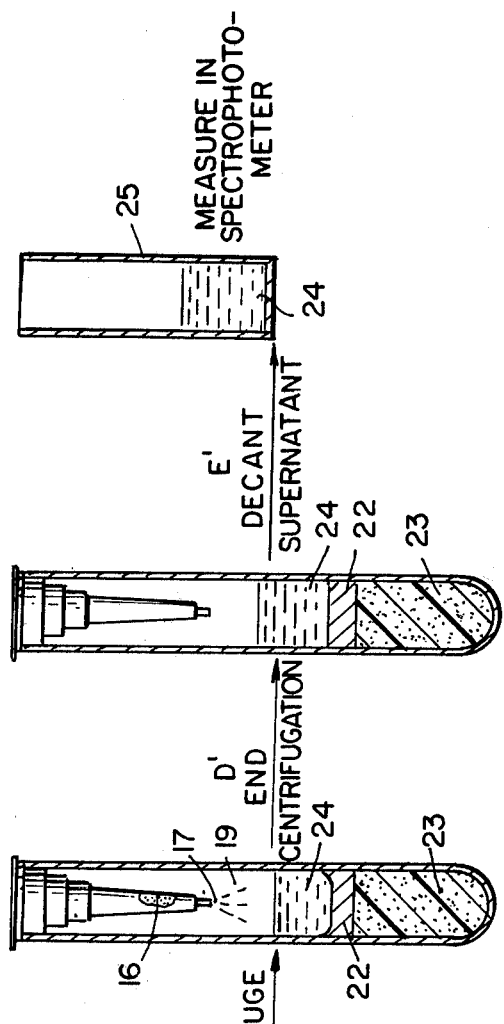
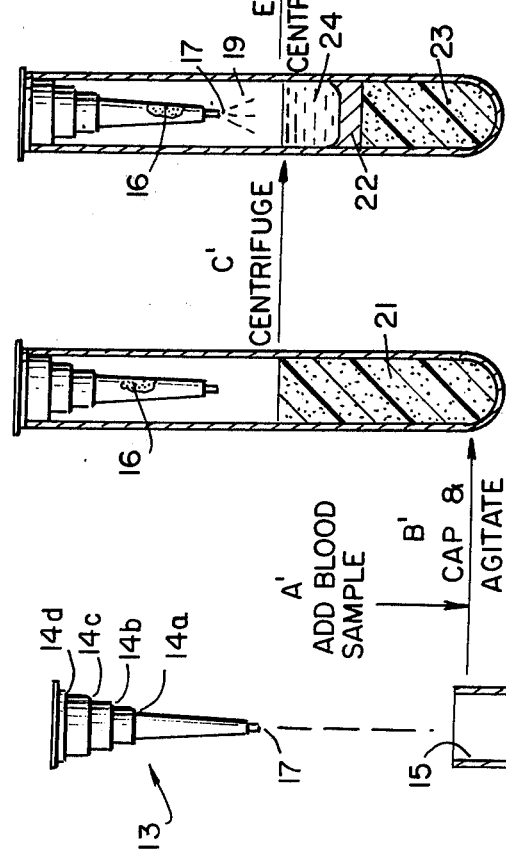
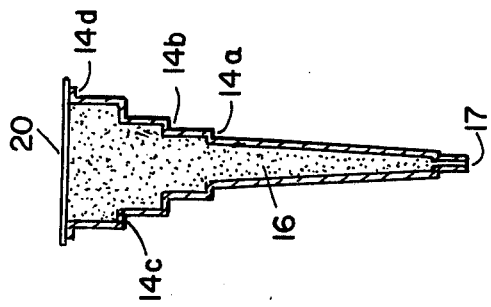

METHOD AND APPARATUS FOR GLYCOSYLATED HEMOGLOBIN SEPARATING AND MEASURING FRACTIONS

FIELD OF THE INVENTION

This invention relates to a method and apparatus for treating a mammalian blood sample. More specifically, this invention relates to a method and apparatus for separating and measuring the glycosylated hemoglobin blood fraction in a blood sample.

BACKGROUND OF THE INVENTION

The prior art provided various methods and apparatus for measuring the concentration of glycosylated hemoglobin in a blood sample. These methods principally required microcolumn devices for chromatographic separation of the blood sample fractions. Typically, the blood samples were separately lysed before passage through the microcolumn. The microcolumn contained an ion exchange resin that binds and separates the various hemoglobin fractions released by lysis of the blood cells as the lysate passes through the column.

For instance, U.S. Pat. No. 4,270,921 to Grass, issued June 2, 1981 relates to a microchromatographic device and a method for determining the relative concentration of glycosylated hemoglobin present in the red blood cells of a person. This reference discloses the use of a microcolumn device which contains an eluent buffer containing a blood cell lysing agent and an ion exchange resin capable of separating out the glycosylated hemoglobin species present in the blood cell lysate. Although both of these components are enclosed within the device, they perform their functions at different locations, with the lysis of the blood cells taking place before the lysate passes through the resin and out into a separate container.

U.S. Pat. No. 4,238,196 to Acuff et al, granted Dec. 9, 1980, discloses a method for measuring glycosylated hemoglobin utitlizing a liquid chromatographic column wherein the blood cells are lysed prior to passage through the column.

U.S. Pat. No. 4,168,147 to Acuff granted Sept. 18, 1979, and U.S. Pat. No. 4,142,858 to Acuff granted Mar. 6, 1979, also relate to methods for measuring glycosylated hemoglobin in a blood sample by utilizing liquid chromatographic microcolumns.

The prior art has also disclosed other methods which required secondary reactions for measuring the glycosylated hemoglobin content in a blood sample.

U.S. Pat. No. 4,268,270 to Gabbay et al granted May 19, 1981, relates to a method and apparatus for measuring glycosylated hemoglobin content of a blood sample wherein blood cells are first lysed with distilled water prior to analysis and then the glycosylated hemoglobin fraction is oxidized to generate aldehydic compounds. The extent of the presence of generated aldehydic compounds are then measured to indicate the amount of glycosylated hemoglobin present.

The prior art has also disclosed various methods and apparatus whose stated use was limited to separating the components of a whole blood sample the blood cells of which have not been lysed. One particular type of device, which fits onto a test-tube in a cap-like manner, injects a silicone type material into the test tube while the tube containing the blood sample is being centrifuged. The silicone type material acts to form a barrier between the accretion solids forced to the bottom of the tube by the centrifugal force and the liquid supernatant remaining above the solids. Glycosylated hemoglobin, however, cannot be released into the supernatant unless the whole blood is lysed prior to centrifugation and this is not suggested by the prior art. The following references U.S. Pat. Nos. 4,230,584 to Ichikawa et al; 4,140,631 to Okuda et al; and 3,780,935 to Lukas et al, all relate to this type of device for use only with separating a whole blood sample into its component parts, serum and whole red blood cells.

There is now provided by the present invention a method and apparatus for separating and measuring the amount of glycosylated hemoglobin in a blood sample which overcomes the limitations of the prior art.

It is, therefore, an object of the present invention to provide a non-chromatographic apparatus for separating a glycosylated hemoglobin fraction from a blood sample.

It is another object of the present invention to provide a meethod for measuring the amount of a glycosylated hemoglobin in a blood sample which is determinative of the relative amount of said hemoglobin present in the blood sample source.

The aforesaid as well as other objects and advantages will be made more apparent in reviewing the attached drawings and in reading the following description and the adjoined claims.

SUMMARY OF THE INVENTION

Essentially, this invention comprises a method and apparatus for separating the glycosylated hemoglobin fraction from a mammalian blood sample and once separated provides a method for measuring the amount of glycosylated hemoglobin present in the blood sample and, inferentially, the blood sample source. The method and apparatus herein utilize lysis of the blood cells in the sample, ion exchange resin binding of hemoglobin fractions released by lysis and centrifugal separation of the lysate-resin mixture. A permanent separation layer is added to the lysate-resin mixture during centrifugation in order to separate the top, liquid supernatant layer and the bottom layer of accretion solids. The supernatant may then be decanted and measured for glycosylated hemoglobin content.

DESCRIPTION OF THE DRAWINGS

FIGS. 1–1D shows the practice of the separation apparatus invention.

FIG. 2 is a sectional view of the extrusion cap of the separation apparatus of FIG. 1.

DESCRIPTION OF THE PREFERRED EMBODIMENTS

Broadly speaking, one preferred embodiment of the present invention is a blood fraction separation apparatus. More specifically, this invention comprises an apparatus for separating glycosylated hemoglobin fractions from a sample of whole blood comprising:
a. a container for holding a blood sample;
b. an ion exchange resin disposed within the container; and
c. a blood cell lysing compound disposed within the container.

Referring to FIG. 1, the separation apparatus herein preferably comprises a test-tube 10 partially filled with a compound 11 comprising an ion exchange resin and red blood cell lysing compound. Compound 11 is preferably disposed substantially adjacent to the bottom or closed end of the test-tube. The separation apparatus may also comprise a cap 13 which is removably attachable to the open end of the separation apparatus test-tube. Preferably, the cap is structured so as to cover and seal the top open end of the test-tube and is formed substantially adjacent to its base to fit the top of the inside wall 15 of the separation apparatus test-tube. The cap tapers down to an open ended nozzle-like configuration within the tube. Referring to FIG. 2, the cap 13 is shown to be formed with a hollow interior which is preferably filled with a viscous polymeric material 16 such as a silicone type of composition. In the practice of this invention, specifically during centrifugation, this silicone type of material is drawn through a hole 17 formed on the cap nozzle or apex and into the test-tube where it acts to separate the supernatant from accretion solids.

Referring to FIG. 1, the lower half of the preferred separation apparatus generally indicated as 10, is shown as a test-tube partially filled with a resin slurry 11. The test-tube 12 is preferably a polypropylene plastic, but may also be other types of plastic or glass and is preferably approximately 12 mm in diameter×75 mm in length. It is preferred that a test-tube of this size contains approximately 4 ml. of the resin slurry 11, although it is foreseeable that larger test-tubes or other forms of containers may be used with a proportionately greater amount of resin slurry.

The term resin slurry, as used herein, is preferably a 25% by volume conditioned resin by volume slurry which comprises about 25% resin and 75% elution lysing buffer by volume (a volume ratio between the two of 1:3). The resin is preferably a conditioned carbon exchange resin such as Biorex 70 (manufactured by Bio Rad Laboratories). The pH of the resin may range from about 6 to 7, more specifically, from 6.76–6.78 and is preferably 6.77±0.01. In addition, the resin is preferably an acrylic type (carboxylic), with a 200–400 wet mesh range (sieve size). The elution lysing buffer as used herein preferably comprises sodium phosphate with potassium cyanide and a surfactant which acts as the hemolysing agent in the practice of the invention. The surfactant is preferably Triton X-100 (manufactured by Rohm and Haas) otherwise known as octyl phenoxy polyethoxyethanol.

Also referring to FIGS. 1 and 2, the upper half of the separation apparatus, a shaped conical cap is shown, generally indicated as 13. Each of the steps or ledges 14a, 14b, 14c and 14d permit the cap to fit into test-tubes, such as 12, that have different diameters and yet still form a seal when disposed adjacent to the inside surface 15 of the test tube 10. The stepped ledges are, however, not necessary for the practice of the invention but merely permit a greater variety of test-tube diameters to be used. The cap is filled with a silicone type material 16 which is extruded from opening 17 formed at the apex of the cap when the cap is disposed inside the test-tube 10 as shown in FIGS. 1A–1C, and the test-tube is subjected to centrifugal force FIG. 1B, said force being directed towards the bottom 18 of the test-tube 10. The extrusion of this material is generally indicated in FIG. 1B by 19. The silicone type material may be of a kind known in the art such as those disclosed in U.S. Pat. Nos. 4,230,584 to Ichikawa et al.; 4,140,631 to Okuda et al; 3,963,119 to Lukacs et al; and 3,780,935 to Lukacs et al. After filling the cap 13 with the silicone-type material, the end opposite hole 17 may be covered or sealed with material 20 so as to prevent possible contamination of the silicone-type material or possible loss of its volatile solvents. The cap 13 is preferably constructed of a one piece molded plastic.

Broadly speaking, one other preferred embodiment of the present invention comprises a method for separating the glycosylated hemoglobin fraction from a mammalian blood sample and a method for measuring the relative amount of said fraction present in the blood sample and, inferentially, the blood sample source, once it is separated from the other hemoglobin fractions.

More specifically, this invention comprises a method for separating glycosylated hemoglobin from a sample of whole blood fluid comprising:

a. providing a quantity of a cation exchange resin to a container (typically one part by volume);

b. providing a quantity of a blood cell lysing composition to said container (typically three parts by volume);

c. providing a quantity of a whole blood sample to said container (typically ten parts by volume);

d. agitating said container for a period of time, and e. providing a settling period for said container after agitation, whereby during agitation the blood cells of said sample are lysed by the blood cell lysing composition, glycosylated hemoglobin is released from said lysed blood cells and goes into suspension in the blood sample fluid, the remaining hemoglobin from said lysed blood cells binds with the cation exchange resin suspended in the blood sample fluid and settles to the bottom of said container with the other blood cell fragments during the settling period, and the glycosylated hemoglobin remains separately in suspension in the blood sample fluid.

As shown in the drawings at step A', the method of separation comprises adding a specified quantity of a blood to the separation apparatus 10 of FIG. 1 which contains the conditioned cation exchange resin and a lysing compound 11. The amount of a blood sample added to the separation apparatus 10 is preferably 5μ. when 4 ml. of resin and lysing agent is used (a proportion, respectively, of about 800:1). The complete method is illustrated in FIGS. 1A–1C. Referring to step A', the blood sample is first added to the test-tube or separation apparatus 10 which is then capped at step B' with cap 13 and then agitated in FIG. 1A. During agitation (by hand, mechanical shaking or rotation) the resin and lysing buffer in the separation apparatus is resuspended into the blood sample liquid, the blood cells are lysed or hemolysed, any glycosylated hemoglobin present in the lysed blood cells is released into the surrounding liquid and hemoglobin fractions other than glycosylated hemoglobin (henceforth, $HA_1$) are absorbed onto the cation exchange resin. The mixture resulting from this agitation is generally indicated as 21. The mixture is preferably agitated for about 10 minutes at about 23° C. although it is envisioned that other times and temperatures may be used effectively. After agitation, the separation apparatus 10 is preferably subjected to centrifugation, indicated at step C', for about 10 minutes at about 23° C. Preferably, the centrifugation is at high speeds, producing a force of 500x g. The term "g" as used herein equals $1.12 \times 10^{-5} \times [RPM]^2 \times radius$, the radius being the distance (cm) from the centrifuge axis to the top of the test tube. During centrifugation the cation exchange resin, blood cell fragments and other solids are forced towards the bottom of the test tube by the centrifugal force as shown in FIG. 1B. Concurrently, the silicone type material is drawn from the hole 17 formed on the cap nozzle by the centrifugal force to form a separation layer 22 between the solids 23 (accretion solids) at the bottom of the tube and the liquid supernatant 24 at the top of the tube. After centrifugation has been completed, indicated at step D', the supernatant 24, which contains the $HA_1$ fraction, is completely separated from the accreted solids 23 by the separation layer 22 and may then, after removing cap 13, be easily decanted at step E' into container 25 of FIG. 1 without fear of contamination by the accretion solids 23. Once decanted, it is now possible with the method described below to measure the supernatant in a spectrophotometer for $HA_1$. It is foreseeable that if test-tube 12 is optically clear it may be possible to measure the supernatant directly, without having to decant.

Generally speaking, the method shown in FIGS. 1-1D is used in order to determine the percent of $HA_1$ out of the total hemoglobin present in the blood system of the source of the blood sample. This method compares the spectrophotometric reading of the supernatant 24 derived from the separation method of FIGS. 1-1C, with the spectrophotometric reading of a diluted whole blood sample taken at the same time and from the same blood source as that which is added to the separation method at step A'.

Essentially, this method provides a way of measuring the amount of glycosylated hemoglobin out of the total hemoglobin in a blood sample comprising:

a. adding a cation exchange resin and a blood cell lysing composition to a first container;
b. adding a first blood sample to the first container;
c. agitating the mixture of step b for a period of time;
d. after agitation exposing the container to centrifugal force for a period of time to form supernatant and accretion solids;
e. providing during exposure to centrifugal force a material which forms a separation layer between the supernatant and accretion solids;
f. measuring the supernatant with a spectrophotometer to obtain a first measurement;
g. adding a second blood sample to a quantity of water in a second container;
h. measuring the mixture of step g, with a spectrophotometer to obtain a second measurement; and
i. measuring the difference between the first measurement and the second measurement, whereby the ratio of said first measurement to said second measurement is indicative of the relative amounts of glycosylated hemoglobin out of the total hemoglobin of the blood sample.

The supernatant 24, as shown in FIG. 1D is measured in a spectrophotometer or colorimeter at about 415 nm to give a specific reading "X". A second whole blood sample, preferably about 5μ, which was taken from the same source as the first blood sample and at the same time, is diluted into about 20 ml. of water (a proportion of about 1:4000). The diluted whole blood sample is then measured in a spectrophotometer or colorimeter at about 415 nm to give a specific reading "A". The approximate percent of $HA_1$ present out of the total hemoglobin is equal to the ratio of the first reading "X" over the second reading "A" multiplied by $6.66 \pm 01$.

The practice of the methods disclosed herein with the apparatus disclosed herein may be simply and accurately performed within a matter of minutes and with a minimum of steps. In addition, it is foreseeable that pre-filled separation device test-tubes can be prepared containing the conditioned resin slurry and possibly marked with indicia indicating desired fluid levels. These pre-filled test-tubes may also be supplied with the extrusion type cap so as to form the preferred separation device.

In the specification herein, there have been set forth preferred embodiments of the invention, and although specific terms are employed, they are used in a generic and descriptive sense only and not for purposes of limitation.

Inasmuch as many changes could be made in the above construction, and many apparently different embodiments of the invention could be made without departing from the scope thereof, it is intended that all matters contained in the above description shall be interpreted as illustrative and not in a limiting sense.

What is claimed is:

1. An apparatus for separating glycosylated hemoglobin fractions from a sample of whole blood comprising:
   a. a container for holding said blood sample; said container being formed with one open end and one closed end;
   b. an ion exchange resin disposed within said container and substantially adjacent to said closed end;
   c. a blood cell lysing compound disposed within said container and substantially adjacent to said closed end; and
   d. a cap, said cap being removably attachable to said open end and forming a sealed container when attached; said cap being formed with a substantially conical shape and having an opening at the apex of the cone; said conical cap depending into said container and with the interior of said conical cap containing a viscous polymeric material.

2. The apparatus of claim 1, wherein the viscous polymeric material comprises a silicone type of material.

3. The apparatus of claim 1, wherein the diameter of the cap adjacent to the base of the cone is substantially similar to that of the diameter of the inside of the cylinder.

4. The apparatus of claim 1, wherein the container is cylindrical.

5. The apparatus of claim 4, wherein the container is a test tube.

6. The apparatus of claim 1, wherein the cation exchange resin is mixed with the blood lysing compound to form a mixture in the container.

7. The apparatus of claim 6, wherein the volume ratio of the volume mixture of cation exchange resin to blood lysing compound is about 1:3.

8. The apparatus of claim 1, wherein the ion exchange resin is a cation exchange resin.

9. The apparatus of claim 8, wherein the cation exchange resin is an acrylic type.

10. The apparatus of claim 8, wherein the cation exchange resin has a pH of about 6 to about 7.

11. The apparatus of claim 8, wherein the cation exchange resin has a 200-400 wet mesh range.

12. The apparatus of claim 1, wherein the blood cell lysing compound comprises a elution lysing buffer.

13. The apparatus of claim 12, wherein the elution lysing buffer comprises sodium phosphate, potassium cyanide and a surfactant.

14. The apparatus of claim 12, wherein the surfactant is a hemolysing agent.

15. The apparatus of claim 12, wherein the surfactant is octyl phenoxy polyethoxyethanol.

16. A method for separating glycosylated hemoglobin from a sample of whole blood fluid comprising:
   a. providing a quantity of a cation exchange resin to a container;
   b. providing a quantity of a blood cell lysing composition to said container;
   c. providing a quantity of blood sample to said container;
   d. agitating said container for a period of time;
   e. providing said container with a quantity of a viscous polymeric material during agitation; and
   f. providing a settling period for said container; whereby during agitation the blood cells of said sample are lysed by the blood cell lysing composition, glycosylated hemoglobin is released from said lysed blood cells and goes into suspension in the blood sample fluid, the remaining hemoglobin from said lysed blood cells binds with the cation exchange resin suspended in the blood sample fluid and settles to the bottom of said container with the other blood cell fragments during the settling period, and the glycosylated hemoglobin remains separately in suspension in the blood sample fluid, said viscous polymeric material providing a permanent barrier between settled solids and the glycosylated hemoglobin in the blood sample fluid.

17. The method of claim 16, wherein the container is agitated for about 10 minutes at about 23° C.

18. The method of claim 16, wherein the viscous polymeric material is a silicone type of material.

19. The method of claim 16, wherein the container is provided with a volume ratio of cation exchange resin to blood cell lysing composition to whole blood fluid of about 1:3:10.

20. The method of claim 19, wherein the container is a test-tube.

21. The method of claim 16, wherein the container is exposed to centrifugal force to decrease the time needed for the settling period.

22. The method of claim 21, wherein the container is exposed to about 10 minutes of centrifugation at high speeds.

23. The method of claim 22, wherein the viscous polymeric material is a silicone type of material.

24. The method of claim 16, wherein the blood cell lysing composition is an elution lysing buffer.

25. The method of claim 24, wherein the elution lysing buffer comprises sodium phosphate, potassium cyanide and a surfactant.

26. The method of claim 25, wherein the surfactant is a hemolysing agent.

27. The method of claim 25, wherein the surfactant is octyl phenoxy polyethoxyethanol.

28. A method for measuring the amount of glycosylated hemoglobin out of the total hemoglobin in a blood sample comprising:
   a. adding a cation exchange resin and a blood cell lysing composition to a first container;
   b. adding a first blood sample to the first container;
   c. agitating the mixture of step b for a period of time;
   d. after agitation, exposing the container to centrifugal force for a period of time to form supernatant and accretion solids;
   e. providing a viscous polymeric material which forms a separation layer between the supernatant and accretion solids during exposure of said centrifugal force;
   f. measuring the supernatant with a spectrophotometer to obtain a first measurement;
   g. adding a second blood sample to a quantity of water in a second container;
   h. measuring the mixture of step g, with a spectrophotometer to obtain a second measurement; and
   i. measuring the difference between the first measurement and the second measurement whereby the ratio of said first measurement to said second measurement is indicative of the relative amounts of glycosylated hemoglobin out of the total hemoglobin of the blood sample.

29. The method of claim 28, wherein the mixture is agitated for about 10 minutes.

30. The method of claim 28, wherein the mixture is centrifuged at high speeds for about 10 minutes.

31. The method of claim 28, wherein the supernatant is measured in a spectrophotometer at about 415 nm.

32. The method of claim 28, wherein the quantity of the second blood sample is about 5μ.

33. The method of claim 28, wherein the quantity of water in step g is about 20 ml.

34. The method of claim 28, wherein the ratio of the spectrophotometric reading of the first blood sample to the spectrophotometric reading of the second blood sample multiplied by 6.66±0.01 equals the percentage of glycosylated hemoglobin out of the total hemoglobin present.

35. The method of claim 28, wherein the viscous polymeric material is a silicone type of material.

36. The method of claim 28, wherein the quantity of first blood sample is about 5μ.

37. The method of claim 36, wherein the total quantity of the cation exchange resin and a blood cell lysing composition is about 4 ml.

* * * * *